US006858438B2

(12) United States Patent
Van Venrooij et al.

(10) Patent No.: US 6,858,438 B2
(45) Date of Patent: Feb. 22, 2005

(54) PEPTIDES IMMUNOREACTIVE WITH AUTOANTIBODIES FROM PATIENTS WITH RHEUMATOID ARTHRITIS

(75) Inventors: Waltherus Jacobus Wilhelmus Van Venrooij, Nijmegen (NL); Jozef Maria Hendrik Raats, Nijmegen (NL); Rene Michael Antonius Hoet, Nijmegen (NL); Gerardus Antonius Schellekens, Den Bosch (NL)

(73) Assignee: Stichting Voor De Technische Wetenschappen, Utrecht (NL)

( * ) Notice: Subject to any disclaimer, the term of this patent is extended or adjusted under 35 U.S.C. 154(b) by 0 days.

(21) Appl. No.: 09/308,150

(22) PCT Filed: Nov. 14, 1997

(86) PCT No.: PCT/NL97/00624

§ 371 (c)(1),
(2), (4) Date: Sep. 30, 1999

(87) PCT Pub. No.: WO98/22503

PCT Pub. Date: May 28, 1998

(65) Prior Publication Data

US 2002/0137092 A1 Sep. 26, 2002

(30) Foreign Application Priority Data

Nov. 15, 1996 (NL) .............................. 1004539

(51) Int. Cl.⁷ ...................... G01N 33/53; G01N 33/564; C07K 7/08; C07K 16/18
(52) U.S. Cl. ...................... 436/509; 435/7.1; 435/7.92; 530/326; 530/388.25; 530/389.3
(58) Field of Search .................... 530/388.25, 389.3, 530/300, 317, 324; 435/7.92, 7.1, 7.21; 436/506, 509

(56) References Cited

U.S. PATENT DOCUMENTS 5,888,833 A * 3/1999 Serre et al.

FOREIGN PATENT DOCUMENTS

WO    WO/95 34312    * 12/1995
WO    WO99/35617     * 7/1999

OTHER PUBLICATIONS

Abaza et al., J. Biol. Chem. 11(5):433–444, 1992.*
Tarsca, E et al. J. Biol. Chem. (Nov., 1996) 271(48):30709–30716.*
Girbal–Neuhauser, Elisabeth, et al., "The Epitopes Targeted by the Rheumatoid Arthritis–Associated Antifilaggrin Autoantibodies are Posttranslationally Generatedon Various Sites of (Pro)Filaggrin by Deimination of Arginine Residues," J of Immunology, vol. 162, pp 585–594 (1999).

Schellekens, G.A., et al., "Citrulline is an Essential Constituent of Antigenic Determinants Recognized by Rheumatoid Arthritis–Specific Autoantibodies," J. Clin. Invest. vol. 101, No. 1, pp 273–281 (Jan. 1998).

Shellekens, G.A., et al., "The Diagnostic Properties of Rheumatoid Arthritis Antibodies Recognizing a Cyclic Citrullinated Peptide," Arthritis & Rheumatism, vol. 43, No. 1, pp 155–163 (Jan. 2000).

Van Jaarsveld, C.H.M., et al., "The Prognostic Value of the Antiperinuclear Factor, Anti–Citrullinated Peptide Antibodies and Rheumatoid Factor in Early Rheumatoid Arthritis," Clinical and Experimental Rheumatology vol. 17, pp 689–697 (1999).

Gan, Song–Qing, "Organization, Structure, and Polymorphisms of the Human Profilaggrin Gene," Biochemistry, vol. 29, No. 40, pp 9432–9440 (Oct. 9, 1990).

Hoet, R.M.A., et al., "Antiperinuclear Factor, a Marker Autoantibody for Rheumatoid Arthritis: Colocalixstion of the Perinuclear Factor and Profilaggrin," Annals of the Rheumatic Diseases, vol. 50, No. 9, Loden, Great Britain (Sep. 1991)p. 611–614.

Misaki, Y., et al., "The 56K Autontigen is Identical to Human Annexin XI", Journal of Biological Chemistry, vol. 269, No. 6, Baltimore MD, pp 4240–4246 (Feb. 11, 1994).

Seggag, M., et al., "The Antiperinuclear Factor and the So–Called Antikeratin antibodies Are the Same Rheumatoid Arthritis—Specific Autoantibodies," Journal of Clinical investigation, vol. 95, No. 6, New York NY (Jun. 1995) p 2672–2679.

Simon, M., et al., "The Cyokeratin Filament–Aggregating Protein Filaggrin is the Target of the So–called 'Antikeratin Antibodies,' Autoantibodies Specific for Rheumatoid Arthritis," Journal of Clinical Investigation, vol. 92, No. 3, pp 1387–1393 New York NY (Sep. 1993).

Shellenkens, G.A., et al., "The Modified Arginine residue Citrulline is the Major Constituent of Epitopes Recognized by Autoantibodies in Sera from Rheumatoid Arthritis Patients," Arthritis and Rheumatism, vol. 40, No. 9, p. S276, New York NY (Nov. 8–12, 1997).

* cited by examiner

Primary Examiner—Christina Chan
Assistant Examiner—F. Pierre VanderVegt
(74) Attorney, Agent, or Firm—Morrison & Foerster LLP

(57) ABSTRACT

The invention relates to a peptide derived from an antigen recognized by autoantibodies, which peptide is reactive with autoimmune antibodies from a patient suffering from rheumatoid arthritis. The peptide according to the invention possesses a modified arginine residue. The invention also relates to antibodies against the peptide and a method of detection autoimmune antibodies.

5 Claims, 1 Drawing Sheet

FORMULA SHEET

I $$\begin{array}{c} \overset{NH_2}{X} \quad Y \\ \diagdown \quad \diagup \\ C \\ | \\ Z\text{-NH} \\ | \\ (CH_2)_n \\ | \end{array}$$

| | | |
|---|---|---|
| II | S H Q E S T X G R S R G R S G R S G S | SEQ ID NO 1 |
| III | S H Q E S T R G X S R G R S G R S G S | SEQ ID NO 2 |
| IV | S H Q E S T R G R S X G R S G R S G S | SEQ ID NO 3 |
| V | S H Q E S T R G R S R G X S G R S G S | SEQ ID NO 4 |
| VI | S H Q E S T R G R S R G S X S G S | SEQ ID NO 5 |
| VII | S H Q E S T X G X S R G R S G R S G S | SEQ ID NO 6 |
| VIII | S H Q E S T X G R S X G R S G R S G S | SEQ ID NO 7 |
| IX | S H Q E S T X G R S R G X S G R S G S | SEQ ID NO 8 |
| X | S H Q E S T X G R S R G R S G X S G S | SEQ ID NO 9 |
| XI | H Q C H Q E S T X G R S R G R C G R S G S | SEQ ID NO 10 |

SEQUENCE LISTING

```
<160> NUMBER OF SEQ ID NOS:  16

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 1

Ser His Gln Glu Ser Thr Xaa Gly Arg Ser Arg Gly Arg Ser Gly Arg
  1               5                  10                  15

Ser Gly Ser

<210> SEQ ID NO 2
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 2

Ser His Gln Glu Ser Thr Arg Gly Xaa Ser Arg Gly Arg Ser Gly Arg
  1               5                  10                  15

Ser Gly Ser

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 3

Ser His Gln Glu Ser Thr Arg Gly Arg Ser Xaa Gly Arg Ser Gly Arg
  1               5                  10                  15

Ser Gly Ser

<210> SEQ ID NO 4
<211> LENGTH: 19
<212> TYPE: PRT
<213> ORGANISM: Artificial Sequence
<220> FEATURE:
```

-continued

```
<223> OTHER INFORMATION: Description of Artificial Sequence:Derived from
      known cDNA sequences of human profilaggrin
<223> OTHER INFORMATION: Xaa is citrulline

<400> SEQUENCE: 4

Ser His Gln Glu Ser Thr Arg Gly Arg Ser Arg Gly Xaa Ser Gly Arg
 1               5                  10                  15

Ser Gly Ser

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 5

Ser His Gln Glu Ser Thr Arg Gly Arg Ser Arg Gly Arg Ser Gly Xaa
 1               5                  10                  15

Ser Gly Ser

<210> SEQ ID NO 6
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 6

Ser His Gln Glu Ser Thr Xaa Gly Xaa Ser Arg Gly Arg Ser Gly Arg
 1               5                  10                  15

Ser Gly Ser

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 7

Ser His Gln Glu Ser Thr Xaa Gly Arg Ser Xaa Gly Arg Ser Gly Arg
 1               5                  10                  15

Ser Gly Ser

<210> SEQ ID NO 8
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 8

Ser His Gln Glu Ser Thr Xaa Gly Arg Ser Arg Gly Xaa Ser Gly Arg
 1               5                  10                  15

Ser Gly Ser
```

```
<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 9

Ser His Gln Glu Ser Thr Xaa Gly Arg Ser Arg Gly Arg Ser Gly Xaa
 1               5                  10                  15

Ser Gly Ser

<210> SEQ ID NO 10
<211> LENGTH: 21
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline
<221> NAME/KEY: DISULFID
<222> LOCATION: (3)..(16)

<400> SEQUENCE: 10

His Gln Cys His Gln Glu Ser Thr Xaa Gly Arg Ser Arg Gly Arg Cys
 1               5                  10                  15

Gly Arg Ser Gly Ser
             20

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin

<400> SEQUENCE: 11

Ser His Gln Glu Ser Thr Arg Gly Arg Ser Arg Gly Arg Ser Gly Arg
 1               5                  10                  15

Ser Gly Ser

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin

<400> SEQUENCE: 12

Ser His Gln Glu Ser Thr Ala Gly Arg Ser Arg Gly Arg Ser Gly Arg
 1               5                  10                  15

Ser Gly Ser

<210> SEQ ID NO 13
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin

<400> SEQUENCE: 13
```

-continued

```
Ser His Gln Glu Ser Thr Glu Gly Arg Ser Arg Gly Arg Ser Gly Arg
  1               5                   10                  15

Ser Gly Ser

<210> SEQ ID NO 14
<211> LENGTH: 19
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin

<400> SEQUENCE: 14

Ser His Gln Glu Ser Thr Gln Gly Arg Ser Arg Gly Arg Ser Gly Arg
  1               5                   10                  15

Ser Gly Ser

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin
<223> OTHER INFORMATION: Xaa is citrulline

<400> SEQUENCE: 15

Thr Gly Pro Ser Thr Arg Gly Arg Gln Gly Ser Xaa His Glu
  1               5                   10

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence:Derived from
      known cDNA sequences of human profilaggrin

<400> SEQUENCE: 16

Glu Ser Ser His Gly Trp Thr Gly Pro Ser Thr Arg Gly Arg Gln Gly
  1               5                   10                  15

Ser Arg His Glu
            20
```

PEPTIDES IMMUNOREACTIVE WITH AUTOANTIBODIES FROM PATIENTS WITH RHEUMATOID ARTHRITIS

CROSS-REFERENCE TO RELATED APPLICATIONS

This application is a national stage filing under 35 U.S.C. §371 from PCT/NL97/00624, filed 14 Nov. 1997, and claims priority to Netherlands Application No. 1004539, filed 15 Nov. 1996.

BACKGROUND OF THE INVENTION

1. Field of the Invention

The present invention relates to a peptide derived from an antigen recognized by autoantibodies from patients with rheumatoid arthritis, which peptide is reactive with autoimmune antibodies from a patient suffering from rheumatoid arthritis.

2. Description of the Related Art Including Information Disclosed Under 37 C.F.R. §§1.97–1.99.

Such a peptide is known from the European patent application 0 511 116 (Clonatec S. A.). This application describes an antigen comprising a filaggrin or profilaggrin fragment. The peptide is recognized by rheumatoid arthritis-specific autoimmune antibodies. Rheumatoid arthritis (RA) is a systemic autoimmune disease. It is the most commonly occurring inflammatory disease of the joints, it is chronic and may lead to severe physical disablement.

The object of the present is to provide a peptide which is reactive with autoimmune antibodies from a patient suffering from rheumatoid arthritis, which peptide is suitable for diagnostic research with increased specificity while also being useful for other purposes such as obtaining (raising, selecting and isolating) poly- and monoclonal antibodies.

SUMMARY OF THE INVENTION

To this end the peptide according to the invention is characterized in that the derived peptide that is reactive with autoimmune antibodies, corresponds to a part of a mRNA molecule coding for the antigen, said part comprising a codon for an arginine residue, and the arginine residue in the derived peptide, which is reactive with autoimmune antibodies, is a modified arginine residue.

Surprisingly, the peptide according to the invention that possesses a modified arginine residue, proved to be very suitable for the specific diagnosis of rheumatoid arthritis.

BRIEF DESCRIPTION OF THE DRAWING

FIG. 1 depicts formulas of this invention.

DESCRIPTION OF THE PREFERRED EMBODIMENTS

To this day, no specific serological test is available for RA. The only test frequently employed is based on the determination of rheumatoid factors (Rf; Ref. 1) which are found in 70% of the RA patients. However, this test is not very specific and is characterized by a relatively large number of false positives. For patients suffering from systemic lupus erythematosus the percentage of false positives is approximately 20% and for healthy individuals approximately 5%.

Preferably the peptide is characterized in that the modified arginine residue's side chain is a side chain according to Formula I on the formula sheet, in which $X=NH_2$, $CH_3$, $NHCH_3$ or $N(CH_3)_2$;
$Y=O$, $NH$, $NHCH_3$ or $N(CH_3)_2$;
$Z=O$, $NH$, or $CH_2$; and
$n=2$, 3 or 4, on the condition that when $X=NH_2$ and $Z=NH$, $Y$ is not $NH$; and the modified arginine residue is in particular a citrulline residue. For citrulline, $X=NH_2$, $Y=O$, $Z=NH$ and $n=3$.

A preferred peptide is the peptide selected from the group of peptides having the Formula II-X on the formula sheet.

By using the peptide according to Formula II, it is possible to establish the presence of rheumatoid arthritis in about 36% of patients actually suffering from rheumatoid arthritis, while the percentage of false positives for other autoimmune diseases and healthy individuals is less than 2%.

According to a favourable embodiment the peptide is a cyclic peptide, for instance, due to the presence of a cystine residue.

In some cases such a cyclic peptide exhibits an increased immunological affinity.

The preferred cyclic peptide is the peptide having the Formula XI on the formula sheet.

Preferably the peptide is a synthetic peptide.

The reactive peptide according to the invention can be obtained pure and in large quantities by means of organic synthesis, making immunological testing on a large scale possible.

According to an alternative embodiment, the peptide in accordance with the invention is characterized in that the peptide is obtained by the proteolytic treatment of (pro) filaggrin, separation of peptide fragments formed by proteolysis and subsequent selection on the presence of a modified arginine residue in a peptide which was formed during the proteolytic treatment.

In this manner peptides can be identified which can increase the sensitivity of a rheumatoid arthritis test. The term sensitivity is in the present application to be understood to mean the ability of a test to properly identity a patient suffering from rheumatoid arthritis.

According to a favourable embodiment, the antigen is (pro) filaggrin, and the peptide is reactive with a rheumatoid arthritis patient's autoimmune antibodies which are reactive with (pro)filaggrin.

The peptide has been shown to be very suitable for high-specificity testing (few false positives) for rheumatism, The present invention also relates to an antibody which is cross-reactive with an antibody raised against a peptide according to the invention.

Such an antibody is useful for the indication of rheumatoid arthritis by analysing sections of biopsy samples and immunological tests of the sandwich type.

The antibody is preferably a monoclonal antibody.

According to another preferred embodiment, the antibody is obtained by using as antigen a peptide in accordance with the invention.

A suitable antibody according to the invention is characterized in that it is cross reactive with the antibody as produced by *Escherichia coli* TG1 with plasmid RA3, deposited at the Centraalbureau voor Schimmelcultures, at Baarn, the Netherlands under accession number CBS143.96.

The invention further relates to an organic compound comprising a part that is able to compete with a peptide according to one of the claims 1 to 9 for binding to an antibody which is specific for said peptide, wherein at least said part of the organic compound can be prepared by means of combinatorial chemistry.

Such organic compounds are found by competitive selection wherein a peptide of the invention competes for recognition by an antibody of the invention, such as the antibody produced by *E. coli* CB143.96. The organic compounds, which are often cheaper to produce than antigens that are prepared solely on the basis of amino acids that may or may not comprise side chains, are suitable for immunological kits for diagnosing RA. Also, after coupling to a solid carrier, said organic compounds could be applied to lower, through adsorption, the level of autoimmune antibodies in the blood of patients suffering from RA.

Finally, the invention relates to a method of detecting autoimmune antibodies against rheumatoid arthritis.

The method according to the invention is characterized in that in an immunological test at least one immunologically active molecule selected from the group consisting of i) a peptide according to the invention; ii) a combinatorial organic molecule according to the invention; and iii) an antibody according to the invention is used.

In addition to increased sensitivity other advantages are achieved, in particular better reproducibility quantitative information and better applicability for prognostic purposes.

To a person skilled in the art it will be apparent that there are a number of possible variations to the present invention as specified by the appended claims. For instance, the peptides mentioned on the formula sheet may also be part of other oligopeptides. They may be provided at one or both ends with one or more other amino acids while also, two or more peptides according to the invention may be part of one oligopeptide. It is also possible to shorten the peptides by one or more amino acids, provided this does not have a significantly adverse effect on the reactivity. The expert is familiar with the manner in which peptides and organic compounds according to the invention may optionally be labelled or be coupled to a carrier, and how on the basis of such antigens an immunological test may be developed, using the standard techniques well-known in the field.

The invention will now be explained in more detail by means of the following example.

Materials and Methods

Peptide synthesis: Peptides were selected for synthetic on the basis of amino acid sequences derived from known cDNA sequences of human profilaggrin (Ref. 3; Ref. 3). The peptides were synthesized on solid phase using the method described by Schellekens et al. (Ref. 4). The peptides were at least 95% pure, as determined by the elution profile by means of reversed phase chromatography and the relative absorption at 214 nm. The composition of the peptides was confirmed by means of mass spectrometry (MALDI-MS). All peptides were synthesized as peptide amides.

TABLE 1

Synthesized peptides
The peptide names starting with "cf" are based on the C-terminal end (amino acids 306–324); and the peptide names starting with "nf" are based on the sequence near the N-terminal end (amino acido 18 32 for nfc1). Amino acid sequences based on cDNA of a profilaggrin repeat.

| Name | Peptide sequence* |
|---|---|
| cfc1 SEQ ID NO:1 | S H Q E S T X G R S R G R S G R S G S |
| cfc2 SEQ ID NO:2 | S H Q E S T R G X S R G R S G R S G S |

TABLE 1-continued

Synthesized peptides
The peptide names starting with "cf" are based on the C-terminal end (amino acids 306–324); and the peptide names starting with "nf" are based on the sequence near the N-terminal end (amino acido 18 32 for nfc1). Amino acid sequences based on cDNA of a profilaggrin repeat.

| Name | Peptide sequence* |
|---|---|
| cfc3 SEQ ID NO:3 | S H Q E S T R G R S X G R S G R S G S |
| cfc4 SEQ ID NO:4 | S H Q E S T R G R S R G X S G R S G S |
| cfc5 SEQ ID NO:5 | S H Q E S T R G R S R G R S G X S G S |
| cfc6 SEQ ID NO:6 | S H Q E S T X G X S R G R S G R S G S |
| cfc7 SEQ ID NO:7 | S H Q E S T X G R S X G R S C R S G S |
| cfc8 SEQ ID NO:8 | S H Q E S T X G R S R G X S G R S G S |
| cfc9 SEQ ID NO:9 | S H Q E S T X G R S R G R S G X S G S |
| cf SEQ ID NO:10 | S H Q E S T R G R S R G R S G R S G S |
| cfA SEQ ID NO:11 | S H Q E S T A G R S R G R S G R S G S |
| cfE SEQ ID NO:12 | S H Q E S T E G R S R G R S G R S G S |
| cfQ SEQ ID NO:13 | S H Q E S T Q G R S R G R S G R S G S |
| nfc1 SEQ ID NO:14 | T G P S T R G R Q G S X H E |
| nf SEQ ID NO:15 | E S S H G W T G P S T R G R Q G S R H E |

*(A = alanine; G = glycine; H = histidine; E = glutamic acid; P = proline; R = arginine; Q = glutamine; S = serine; T = threonine; W = tryptophan; X = citrulline)

Detection by Means of ELISA

Via an N-oxysuccinimide surface the peptides were covalently coupled to the wells of 96-well microtiter plates (Costar amide binding plates) in an amount of 1 μg/wall. Coupling took place for 16 hours at 4EC and pH 9.0. The plates wore blocked for 1 hour with 2% bovine serum albumin. The sera were diluted 200 times in a diluent (0.3% BSA, 350 mM NaCl, 10 mM Tris-HCl pH 7.6, 1% vol./vol. Triton X-100, 0.5% w./vol. Na-deoxycholate, 0.1% SDS) supplemented with 10% normal rabbit serum, and incubated for one hour at room temperature. After washing the plates (3 times with PBS containing 0.05% by vol. of Tween®20), 100 μl of antihuman IgG conjugated with peroxidase (Dako P214), 1000 times diluted in dilution buffer, was added to the wells. After incubation for 1 hour at room temperature, the plates were washed 3 times with PBS/Tween®, and bound antibodies were detected with tetramethyl benzidine as a substrate. After 10 minutes the reaction was stopped by adding 100 μl of 2 M sulphuric acid per well. Readout occurred at 450 nm. Sera having an $OD_{450}$ of 0.2, after deduction of the blank for the respective serum (a well without a coupled peptide), were considered to be positive.

Results

The results are listed in Table 2. In total, 288 sera from patients suffering from rheumatoid diseases were used, 132 of which were from patients suffering from rheumatoid arthritis.

TABLE 2

Results with peptide cfc1 to cfc9 (Formula II to X of the formula sheet)

| Peptide | RA sera (%) (n = 134) | control sera[1] (%) (n = 154) | SLE[2] (%) (n = 50) | SSC[3] (%) (n = 50) | pSS[4] (%) (n = 50) | PM/DM[5] (%) (n = 50) |
|---|---|---|---|---|---|---|
| cfc1 | 49 (36) | 1 (0.6) | 1 (2) | 0 | 0 | 0 |
| cfc2 | 27 (20) | 4 (2.6) | 1 (2) | 0 | 1 (2) | 1 (2) |
| cfc3 | 37 (28) | 2 (0.6) | 0 | 0 | 1 (2) | 1 (2) |
| cfc4 | 32 (24) | 2 (1.3) | 0 | 0 | 0 | 0 |
| cfc5 | 64 (48) | 1 (0.6) | 0 | 1 (2) | 2 (4) | 1 (2) |
| cfc6 | 65 (48) | 1 (0.6) | 0 | 0 | 2 (4) | 1 (2) |
| cfc7 | 60 (45) | 1 (0.6) | 0 | 0 | 1 (2) | 1 (2) |
| cfc8 | 55 (41) | 1 (0.6) | 0 | 0 | 1 (2) | 1 (2) |
| cfc9 | 57 (42) | 1 (0.6) | 0 | 0 | 2 (4) | 0 |

[1] Control sera are from patients suffering from rheumatic diseases other then RA.
[2] SLE is systemic lupus erythematosus.
[3] pSS is primary Sjögren's syndrome.
[4] SSC is systemic scleroderma.
[5] PM/DM is polymyositis/dermatomyositis.

Of the total of 134 RA sera from patient's suffering from rheumatoid arthritis, 102 were positive with at least one peptide from the cfc1 to cfc9 series. Therefore, when using these peptides, the sensitivity was 76% (102/134). Of the total of 354 control sera, 13 sera were positive on at least one peptide from the cfc1 to cfc9 series. Therefore the test sensitivity, expressed as percentage of true positives, was 96%. Of the 37 sera that were reactive with cfc3, none were not recognized by peptide cfc1 or cfc23. Of the sera that were reactive with cfc7, cfc8 and cfc9, none were not recognized by cfc1, cfc2, cfc4, cfc5 or cfc6. This means that cfc2, cfc7, cfc8 and cfc9 do not contribute to the test sensitivity and a test sensitivity of 76% may be realized by using the combination of the peptides cfc1, cfc3, cfc4, cfc5 and cfc6.

It should be noted that these percentages depend on the specificity-threshold value applied by applicants. The same data (from the ELISA experiments) can be interpreted as a sensitivity of approximately 80–85% by choosing a slightly lower sensitivity, which incidentally, is still much better than the one obtainable when using the known rheumatoid factor test (Ref. 1).

Sera from patients suffering from various infectious diseases (Borrelia, cyphilis, malaria, endocarditis, Legionella, tuberculosis, mycoplasma, Yezsinia, salmonella, parvovirus B19, Epstein-Barr virus, rubella, schistosomiasis, Toxoplasma, leishmaniasis, Chagas' disease) were tested for the presence of antibodies reactive with cfc1. Of the 308 tested sera 9 were positive. This means that the specificity was 97%, a considerable improvement compared with the RF test.

Variants of cfc1 wherein citrulline was replaced by a neutral (alanine; cfA), acid (glutamic acid; cfE) or amide (glutamine; cfQ) residue, did not seem to be immunologically reactive. The same applies to the control peptide cf, which does not possess a modified arginine residue.

With the aid of the above-described ELISA, a cyclic variant (with the Formula XI on the formula sheet, in which two cysteine residue (C) are bound by means of a sulphur bridge) of cfc1 was tested for 134 RA sera. This cyclic variant was shown to be reactive with 85 sera (63%), signifying an increase in sensitivity. Of the 151 sera of patients suffering from rheumatic diseases other than RA, 3 were shown to be positive (specificity 98%). The priority document of the present application reports 5 falsely determined positives. However, it has been shown that in two of these cases the patients did indeed suffer from RA. Not one serum from 59 healthy individuals was positive with this cyclic peptide, nor with any of the peptides cfc1 to cfc9. The cyclic peptide variant was shown to be reactive with 4 sera of the 200 additional control sera (50 SLE, 50 SCC, 50 pSS, 50 PM/DM) so that the specificity in respect of these sera was 98%. Of the sera from patients suffering from various infectious diseases (308 sera as described above), 7 sera were shown to be positive with the cyclic peptide variant so that in this case also the specificity in respect of these sera was 98%. The use of the cyclic peptide variant thus enhances the sensitivity compared with the individual linear peptide variants, but the specificity is also enhanced due to an improved signal/noise ratio in the described ELISA test.

A second citrulline-substituted peptide (nfc1) was shown to be specifically reactive with 10% of the RA sera, but not with the control peptide nf, which does not comprise citrulline. of the RA sera reactive with nfc1, some were not reactive with cfc1 to cfc9. Therefore, it is possible to increase the sensitivity of a test for rheumatoid arthritis by applying more peptides comprising a modified arginine residue.

Obviously, a peptide may comprise several modified arginine residues, but the peptide may also comprise one or more non-modified arginine residues.

Applicants believe that modified amino acids, in particular those derived from arginine residues, could possibly also play a role in other autoimmune diseases. For this reason, the invention is also aimed at peptides comprising modified amino acids that are reactive with auto-antibodies from patients suffering from autoimmune diseases other than RA. This relates especially to peptides comprising a modified arginine residue wherein X=NHCH$_3$ (wherein Y=NH or NCH$_3$) or NH(CH$_3$)$_2$ is, which peptides will be useful for the detection of autoimmune diseases such as SLE, scleroderma, primary Sjögren's syndrome and polymyositis/dermatomyositis, in which nuclear autoantigens play a role. Said peptides are useful for the development of monoclonal antibodies against these diseases as well as for diagnosing the respective autoimmune diseases, in particular for the detection of autoimmune antibodies in body fluid such as blood, plasma and serum of patients who are suspected of suffering from the autoimmune disease. Again the peptides and antibodies offer the possibility of developing an organic compound with the aid of combinatorial chemistry, which compound is comprised within the scope of the invention.

The recombinant monoclonal antibody described by applicants is reactive with peptide cfc1 but not with the control peptides cfA, cfE, cfQ or cf. The commercially available monoclonal antibody AKH1 (Ref. 5), directed against human filaggrin, is not reactive with any of the peptides described herein and is therefore not cross-reactive with an antibody raised against a peptide according to the invention. The polyclonal serum anti-54 kD (Ref. 5), raised against filaggrin, is not reactive with any of the peptides described herein and is therefore not cross-reactive with an antibody reactive with a peptide according to the invention. This suggests that in a normal immune reaction antibodies that are cross-reactive with an antibody raised against a peptide according to the invention, are not necessarily formed.

REFERENCES

1) Smolen, J. S.,(1996) Autoantibodies in rheumatoid arthritis, in Manual of biological markers of disease (W. J. van Venrooij and R. N. Maini, red.) vol. C Chapter 1.1 pp. 1–18. Kluwer Scientific Publishers, Dordrecht.
2) McKinley-Grant, L. J., Idler, W. W., Bernstein, I. A., Parry, D.A.D., Cannizzaro, L., Croce, C. M., Huebner, K., Lessin, S. R. & Steinert, P. M. (1989) Characterization of a cDNA clone encoding human filaggrin and localization of the gene to chromosome region 1q21. Proceedings of the National Academy of Science U.S.A. 86, pp. 4848–4852.
3) Gan, S. Q., McBride, O. W., Idler, W. W., Nedialka, M. & Steinert, P. M. (1990) Organization, structure, and poly-morphisms of the human profilaggrin gene. Biochemistry 29, pp. 9432–9440.
4) Schellekens, G. A., Lasonder, E., Feijlbrief, M., Kocdijk, D.C.A.M., Drijfhout, J. W., Scheffer, A. J., Welling-Wester, S & Welling, G. W. (1994) Identification of the core residues of the epitope of a monoclonal antibody raised against glycoprotein D of herpes simplex virus 1 by screening of a random peptide library. The European Journal of Immunology 24, pp. 3188–3193.
5) Hoet, R. M. A., Boerbooms, A. A. Th., Arends, M., Ruiter, D. J., van Venrooij, W. J. (1991) Antiperinuclear factor, a marker autoantibody for rheumatoid arthritis: colocalisation of the perinuclear factor and profilaggrin. Annals of the Rheumatic diseases 50, pp. 611–618.

We claim:

1. A purified peptide consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9 and SEQ ID NO:10.

2. The peptide of claim 1 wherein the peptide is immunologically reactive in an immunological assay for detection of rheumatoid arthritis.

3. A method for the detection of rheumatoid arthritis comprising detection of an autoimmune antibody in sera of a patient, comprising the steps of:

contacting the peptide of claim 1 with sera of the patient, and detecting the presence or absence of a complex between said peptide and an antibody, wherein presence of said complex detects rheumatoid arthritis.

4. The method of claim 3, wherein detecting comprises use of an anti-human antibody.

5. The method of claim 3, wherein detecting comprises the use of an enzyme-linked immunosorbent assay (ELISA).

* * * * *